ID: 4,085,118 United States Patent [19]
Pelosi, Jr.
[45] * Apr. 18, 1978

[54] 5-(5-HALOGENATEDPHENYL-2-FURANYL)-DIHYDRO-2(3H)-FURANONES

[75] Inventor: Stanford S. Pelosi, Jr., Norwich, N.Y.

[73] Assignee: Morton-Norwich Products, Inc., Norwich, N.Y.

[*] Notice: The portion of the term of this patent subsequent to Jun. 21, 1994, has been disclaimed.

[21] Appl. No.: 751,279

[22] Filed: Dec. 17, 1976

[51] Int. Cl.$^2$ ............................................ C07D 307/58
[52] U.S. Cl. .................................. 260/343.6; 424/279
[58] Field of Search ........................................ 260/343.6

[56] References Cited

U.S. PATENT DOCUMENTS 4,031,113   6/1977   Pelosi ........................... 260/343.6

OTHER PUBLICATIONS

Houben-Weyl, Methoden der Organischen Chemie, vol. VI/2 (1963), pp. 571–572.

Primary Examiner—Norma S. Milestone
Attorney, Agent, or Firm—Anthony J. Franze

[57] ABSTRACT 5-(5-Halogenatedphenyl-2-furanyl)dihydro-2(3H)-furanones are useful as anti-inflammatory agents.

6 Claims, No Drawings

5-(5-HALOGENATEDPHENYL-2-FURANYL)DIHYDRO-2(3H)-FURANONES

This invention is concerned with chemical compounds and particularly with 5-(5-halogenatedphenyl-2-furanyl)dihydro-2 (3H)-furanones of the formula:

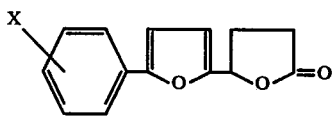

wherein X represents 4-bromo, 3,4-dichloro, 4-fluoro, 2-chloro or 3-chloro.

These compounds possess pharmacological activity. Particularly noteworthy in this respect is their utility to act as antiinflammatory agents as evidenced by their ability to inhibit edema induced by the administration of carrageenin. Thus when they are administered orally at a dose of 300 mg/kg suspended in a vehicle such as aqueous methyl cellulose to rats receiving carrageenin, edema resulting from that substance is inhibited [Winter et al., P.S.E.B.M. 114:544(1964)].

The compounds of this invention can be combined in various pharmaceutical dosage forms such as capsules, tablets, dragees, suspensions and the like using excipients and adjuvants commonplace in the pharmaceutical art and with which there is no incompatibility.

In order that this invention may be readily available to and understood by those skilled in the art, the following examples are supplied.

EXAMPLE I

5-[5-(4-Bromophenyl)-2-furanyl dihydro-2(3H)-furanone

A. Preparation of 4-[5-(4-Bromophenyl)-2-furanyl]-4-oxobutanoic Acid

A mixture of 104 g (0.60 mole) of 4-bromoaniline 200 ml of concentrated hydrochloric acid, and 70 ml of water was heated at 80° for 20 minutes and then cooled to 0°. While maintaining the temperature at 0° a solution of 41 g (0.60 mole) of sodium nitrite in 150 ml of water was added dropwise. The resulting solution was kept at 0° for 30 minutes and then a near solution of 50 g (0.30 mole) of B-(2-furoyl)-propanoic acid in 200 ml of acetone added all at once, followed by a solution of 15 g of $CuCl_2: 2 H_2O$ in 40 ml of water. The bath was removed and the reaction became exothermic reaching a temperature of 36° with a large amount of foaming. The reaction was then warmed on a steam bath for 2 hrs at a temperature of 55°-60°. The reaction was cooled to room temperature and 250 ml of ether was added. The resulting solid was filtered and air-dried to yield 40 g (41%).

B. Preparation of 4-[5-(4-Bromophenyl)-2-furanyl]-4-hydroxybutanoic Acid

A solution of 20 g (0.062 mole) of 4-[5-(4-bromophenyl)-2-furanyl]-4-oxobutanoic acid in 350 ml of 95% dioxane/water was treated portionwise with 5.9 g (0.155 mole) of $NaBH_4$ while maintaining the temperature at 15°-20° by means of an ice bath. The reaction was stirred at ambient temperature for 1 ½ hrs and then filtered. The filtrate was added to ice/$H_2O$ and made acidic with 20% hydrochloric acid. The resulting solid was filtered, dissolved in ethyl acetate (Darco) and refiltered. The filtrate solid was filtered, dissolved in ethyl acetate (Darco) and refiltered. The filtrate was treated with hexane and the resulting solid filtered and air-dried to yield 8 g (40%).

C. Preparation of Title Compound

A mixture of 1.0 g (0.0032 mole) of 4-[5-(4-bromophenyl)-2-furanyl]-4-hydroxybutanoic acid and 25 ml of 10% hydrochloric acid was heated at 50°-55° for 2 hrs and then cooled in an ice bath. The solid was filtered and dissolved in ethyl acetate at room temperature and then treated with hexane. The resulting solid was filtered and dried in the vacuum pistol at room temperature to yield 0.3 g (30%), m.p. 107°-108°.

Anal. Calcd. for $C_{14}H_{11}BrO_3$: C, 54.74; H, 3.61. Found: C, 54.51; H, 3.78.

EXAMPLE II

5-[5-(3,4-Dichlorophenyl)-2-furanyl]dihydro-2(3H)-furanone

A. Preparation of b 4-[5-(3,4-Dichlorophenyl)-2-furanyl]-4-oxobutanoic Acid

A mixture of 97 g (0.60 mole) of 3,4-dichloroaniline, 200 ml of concentrated hydrochloric acid, and 70 ml of water was heated at 80° for 20 minutes and then cooled to 0°. While maintaining the temperature at 0° a solution of 41 g (0.60 mole) of sodium nitrite in 150 ml of water was added dropwise. The resulting solution was kept at 0° for 30 minutes and then a near solution of 50 g (0.30 mole) of B-(2-furoyl) propanoic acid in 200 ml of acetone was added all at once, followed by a solution of 15 g of $CuCl_2.2 H_2O$ in 40 ml of water. The bath was removed and the reaction became exothermic with the temperature being controlled below 50° by means of an ice bath. The reaction was then warmed on the steam bath at 50°-65° for one hr. After standing overnight at room temperature the reaction was treated with 500 ml of ether. The resulting solid was filtered, recrystallized from ethyl acetate and air-dried to yield 8 g (8.5%).

B. Preparation of 4-[5-(3,4-Dichlorophenyl)-2-furanyl]-4-hydroxybutanoic Acid

A mixture of 3.13 g (0.010 mole) of 4-[5-(3,4-dichlorophenyl)-2-furanyl]-4-oxobutanoic acid and 50 ml of 95% dioxane/water was treated portionwise with 0.95 g (0.025 mole) of $NaBH_4$ while maintaining the temperature below 20° by means of an ice bath. The resulting near solution was allowed to stand overnight at room temperature and was then added to ice/water. After acidifying with 20% hydrochloric acid, the resulting oily mixture was extracted with ether and the ethereal extract dried over $MgSO_4$. The ether was removed on a Calab evaporator yielding 3 g (96%) of product as a residual oil.

C. Preparation of Title Compound

A mixture of 3.0 g (0.009 mole) of 4-[5-(3,4-dichlorophenyl)-2-furanyl]-4-hydroxybutanoic acid and 50 ml of 10% hydrochloric acid was heated at 55° for 2½ hrs and then cooled. The resulting solid was filtered, dissolved in ethyl acetate and dried over $MgSO_4$. The $MgSO_4$ was removed by filtration and the filtrate was diluted with hexane. The resulting solid was filtered and dried in the vacuum pistol at room temperature to yield 1.2 g (45%), m.p. 89°-90°.

Anal Calcd. for $C_{14}H_{19}Cl_2O_3$: C, 56.59; H, 3.39. Found: C, 56.51; H, 3.31.

EXAMPLE III

5-[5-(4-Flurophenyl)-2-furanyl]dihydro-2(3H)-furanone

A. Preparation of 4-[5-(4-Fluorophenyl)-2-furanyl]-4-oxobutanoic Acid

A mixture of 58 g (0.52 mole) of 4-fluoroaniline, 175 ml of concentrated hydrochloric acid and 60 ml of water was heated at 80° for 20 minutes and the cooled at 0°. A solution of 36 g (0.52 mole) of sodium nitrite in 200 ml of water was added dropwise while maintaining the temperature at 0°–5°. The resulting near solution was kept at 0° for 30 minutes and then a near solution of 44 g (0.26 mole) of B-(2-furoyl)propanoic acid and 200 ml of acetone was added all at once, followed by a solution of 15 g of $CuCl_2 \cdot 2H_2O$ in 40 ml of water. The bath was removed and the reaction became exothermic with a temperature of 40° being reached. After the exothermicity had ceased, the reaction mixture was heated at 65° for 2 hrs and then allowed to stand overnight at room temperature. The reaction mixture was extracted with ether and the combined ethereal extracts were dried over $MgSo_4$. The ether was removed on a Calab evaporator yielding a residual semi-solid. This material was washed with a minimum amount of ether, washed with hexane and air-dried to yield 16 g (23%).

B. Preparation of 4-[5-(4-Fluorophenyl)-2-furanyl]-4-hydroxybutanoic Acid

A mixture of 13.3 g (0.050 mole) of 4-[5-(4-flurorphenyl)-2-furanyl]-4-oxobutanoic acid and 150 ml of 95% dioxane/water was treated portionwise with 4.8 g (0.125 mole) of $NaBH_4$ at a temperature of 15°–20°. After the addition was completed the reaction was stirred at ambient temperature for 2 hrs and then added to ice/water. The resulting oily mixture was acidified with 20% hydrochloric acid and refrigerated overnight. The resulting solid was filtered, dissolved in ethyl acetate and then diluted with hexane. The resulting solid was filtered and air-dried to yield 3.8 g (29%).

C. Preparation of Title Compound

A mixture of 3.8 g (0.014 mole) of 4-[5-(4-fluorophenyl)-2-furanyl]-4-hydroxybutanoic acid and 60 ml of 10% hydrochloric acid was warmed at 45° for 2 hrs and then cooled in an ice bath. The solid was filtered, washed with water and air-dried to yield 3.3 g (95%). An analytical sample was prepared by dissolving a sample in ethyl acetate (Darco), diluting with hexane and drying the resulting solid in a vacuum pistol at room temperature, m.p. 57°–59°.

Anal. Calcd. for $C_{14}H_{11}FO_3$: C, 68.29; H, 4.50. Found: C, 68.05; H, 4.44.

EXAMPLE IV

5-[5-(2-Chlorophenyl)-2-furanyl]dihydro-2(3H)-furanone

A. Preparation of 4-[5-(2-Chlorophenyl)-2-furanyl]-4-oxobutanoic Acid

A mixture of 77 g (0.60 mole) of 2-chloroaniline, 200 ml of concentrated hydrochloric acid and 70 ml of water was heated at 80° for 20 minutes and then cooled to 0°. A solution of 41 g (0.60 mole) of sodium nitrite in 150 ml of water was added dropwise while maintaining the temperature at 0.5°. The resulting solution was kept at 0° for 30 minutes and then a near solution of 50 g (0.30 mole) of B-(2-furoyl)-propanoic acid in 200 ml of acetone was added all at once, followed by a solution of 15 g of $CuCL_2 \cdot 2H_2O$ in 100 ml of water. The bath was removed and the reaction became exothermic reaching a temperature of 55°. After the exothermicity had ceased, the oily reaction mixture was warmed at 65° for 1½ hrs and then allowed to stand overnight at room temperature. The oily reaction mixture was extracted with ether and the ethereal extract was dried over $MgSO_4$. The ether was removed on a Calab evaporator yielding 102 g of crude product as a residual oil.

B. Preparation of 4-[5-(2-Chlorophenyl)-2-furanyl]-4-hydroxybutanoic Acid

A solution of 102 g (0.30 mole) of the above oil in 1,000 ml of 95% dioxane/water was treated portionwise with 29 g (0.75 mole) of $NaBH_4$ while maintaining the temperature below 20°. After the addition was completed the reaction was stirred at ambient temperature for 2 hrs and then added to ice water. The resulting oily mixture was made acidic with 20% hydrochloric acid and filtered to remove a small amount of solid which was discarded. The filtrate was extracted with ether and the ethereal extract was dried over $MgSO_4$ (Darco). The ether was then removed on a Calab evaporator yielding 84 g of crude product as a residual oil.

C. Preparation of Title Compound

A mixture of 84 g (0.30 mole) of the above oil and 500 ml of 10% hydrochloric acid was heated at 55° for 2½ hrs and then cooled in an ice bath. The aqueous layer was decanted and the residual semi-solid was dissolved in ethyl acetate. The ethyl acetate was dried over $MgSO_4$ and then diluted ca. ten fold with hexane. The organic layer was decanted from a tarry residue and the solvent removed on a Calab evaporator. The resulting oil was triturated in cold ethyl acetate to give a solid. This solid was filtered and air-dried to yield 11 g (14% overall). An analytical sample was prepared by dissolving a sample in ethyl acetate (Darco) and diluting with hexane, m.p. 101°–103°.

Anal. Calcd. for $C_{14}H_{11}ClO_3$: C, 64.01; H, 4.22. Found: C, 64.02; H, 4.30.

EXAMPLE V

5-[5-(3-Chlorophenyl)-2-furanyl]dihydro-2(3H)-furanone

A. Preparation of 4-[5-(3-Chlorophenyl)-2-furanyl]-4-oxobutanoic Acid

A mixture of 77 g (0.60 mole) of 3-chloroaniline, 200 ml of concentrated hydrochloric acid and 70 ml of water was warmed at 80° for 20 minutes and then cooled to 0°. A solution of 41 g (0.6 mole) of sodium nitrite in 150 ml of water was added dropwise while keeping the temperature at 0°–5°. The resulting solution was kept at 0° for 20 minutes. A near solution of 50 g (0.30 mole) of B-(2-furoyl)propanoic acid in 200 ml of acetone was added all at once, followed by a solution of 15 g of $CuCl_2 \cdot 2H_2O$ in 100 ml of water. The bath was removed and the reaction became exothermic with a temperature of 50° being reached. The reaction was stirred at ambient temperature 4 hrs and then ca. 500 ml of ether was added. A small amount of solid was filtered and discarded. The aqueous layer of the filtrate was separated and extracted with ether. The combined ethereal extracts were dried over $MgSO_4$ and the ether was removed on a Calab evaporator. The resulting residual oil was refrigerated overnight, and the solid was filtered, washed with cold ether and air-dried to yield 32 g (38%).

B. Preparation of 4-[5-(3-Chlorophenyl)-2-furanyl]-4-hydroxybutanoic Acid

A solution of 28 g (0.10 mole) of the above solid and 500 ml of 95% dioxane/water was treated portionwise with 9.5 g (0.25 mole) of $NaBH_4$ while maintaining the temperature below 20°. When the addition was completed, the reaction was stirred at ambient temperature for 2 hrs and then added to ice/water. The resulting mixture was made acidic with 20% hydrochloric acid and then extracted with ether. The ethereal extract was dried over MgSO₄ and the ether removed on a Calab evaporator yielding 22 g (79%) of residual oil.

C. Preparation of Title Compound

A mixture of 22 g (0.08 mole) of the above solid and 250 ml of 10% hydrochloric acid was heated at 45° for 2 hrs and then cooled in an ice bath. The aqueous layer was decanted and the residual gummy residue was dissolved in ethyl acetate. The ethyl acetate was dried over MgSO₄ (Darco) and then diluted ca. 10 fold with hexane. After cooling in an ice bath, the solvent was decanted from a tarry residue and then taken to dryness on a Calab evaporator. The resulting oil was dissolved in a minimum amount of ethyl acetate and diluted with hexane. The resulting solid was filtered, washed in cold ether, and air-dried to yield 3.2 g (15%), m.p. 91°-94°.

Anal. Calcd. for $C_{14}H_{11}ClO_3$: C, 64.01; H, 4.22. Found: C, 63.91; H, 4.12.

What is claimed is:
1. A compound of the formula:

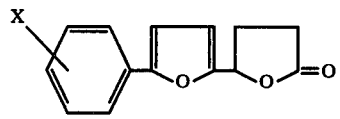

wherein X represents 4-bromo, 3,4-dichloro; 4-fluoro; 2-chloro, or 3-chloro.

2. 5-[5-(4-Bromophenyl)-2-furanyl]dihydro-2(3H)-furanone.

3. 5-[5-(3,4-Dichlorophenyl)-2-furanyl]dihydro-2(3H)-furanone.

4. 5-[5-(4-Fluorophenyl)-2-furanyl]dihydro-2(3H)-furanone.

5. 5-[5-(2-Chlorophenyl)-2-furanyl]dihydro-2(3H)-furanone.

6. 5-[5-(3-Chlorophenyl)-2-furanyl]dihydro-2(3H)-furanone.

* * * * *